(12) United States Patent
Grosse Bley et al.

(10) Patent No.: US 8,633,704 B2
(45) Date of Patent: Jan. 21, 2014

(54) HELIUM SENSOR

(75) Inventors: Werner Grosse Bley, Bonn (DE); Daniel Wetzig, Köln (DE)

(73) Assignee: Inficon GmbH, Cologne (DE)

( * ) Notice: Subject to any disclaimer, the term of this patent is extended or adjusted under 35 U.S.C. 154(b) by 420 days.

(21) Appl. No.: 12/918,948

(22) PCT Filed: Feb. 25, 2009

(86) PCT No.: PCT/EP2009/052225
§ 371 (c)(1),
(2), (4) Date: Aug. 23, 2010

(87) PCT Pub. No.: WO2009/106543
PCT Pub. Date: Sep. 3, 2009

(65) Prior Publication Data
US 2011/0018545 A1  Jan. 27, 2011

(30) Foreign Application Priority Data
Feb. 28, 2008 (DE) .......... 10 2008 011 686

(51) Int. Cl.
*G01N 27/62* (2006.01)
(52) U.S. Cl.
USPC ........................................... 324/464
(58) Field of Classification Search
USPC ........................................... 324/464
See application file for complete search history.

(56) References Cited

U.S. PATENT DOCUMENTS

| 3,141,605 | A | * | 7/1964 | Asamaki | 417/49 |
|---|---|---|---|---|---|
| 3,173,048 | A | * | 3/1965 | Chun | 313/7 |
| 3,241,056 | A | * | 3/1966 | Lawrence, Jr. | 324/466 |
| 3,510,711 | A | * | 5/1970 | Phillips | 417/49 |
| 3,591,827 | A | * | 7/1971 | Hall | 315/108 |
| 3,684,401 | A | | 8/1972 | Singleton | 417/49 |
| 3,684,901 | A | * | 8/1972 | Kroger | 327/584 |
| 3,786,316 | A | * | 1/1974 | Kroger | 257/653 |
| 4,431,709 | A | * | 2/1984 | Bronnes et al. | 428/649 |
| 5,731,584 | A | * | 3/1998 | Beyne et al. | 250/374 |
| 6,285,192 | B1 | * | 9/2001 | Bley et al. | 324/460 |
| 2002/0021068 | A1 | * | 2/2002 | Espinosa | 313/231.61 |
| 2003/0159929 | A1 | * | 8/2003 | Werner | 204/409 |
| 2007/0039377 | A1 | * | 2/2007 | Bohm et al. | 73/40.7 |
| 2007/0286738 | A1 | * | 12/2007 | Lukens | 417/49 |
| 2008/0006080 | A1 | * | 1/2008 | Wetzig | 73/40.7 |
| 2008/0202211 | A1 | * | 8/2008 | Wetzig | 73/40.7 |
| 2009/0178586 | A1 | * | 7/2009 | Bibber | 106/14.25 |

FOREIGN PATENT DOCUMENTS

| DE | 102004034381 | 2/2006 |
|---|---|---|
| DE | 10031882 | 1/2010 |
| GB | 1031766 | 6/1966 |

OTHER PUBLICATIONS

International Search Report for PCT/EP2009/052225 dated May 29, 2009.

* cited by examiner

*Primary Examiner* — Jermele M Hollington
*Assistant Examiner* — Demetrius Pretlow
(74) *Attorney, Agent, or Firm* — Ohlandt, Greeley, Ruggiero & Perle, LLP

(57) ABSTRACT

The helium sensor comprises a housing that encloses a detection chamber. A side of the housing is closed by a permeable wall that is selective for helium. In the detection chamber, there is located an ion getter pump comprising an anode, a cathode and a magnetic field. The cathode, or a cathode leg is made of beryllium. Beryllium has a low atomic mass, whereby the likewise light-weight helium ions can be better incorporated into the cathode material.

13 Claims, 1 Drawing Sheet

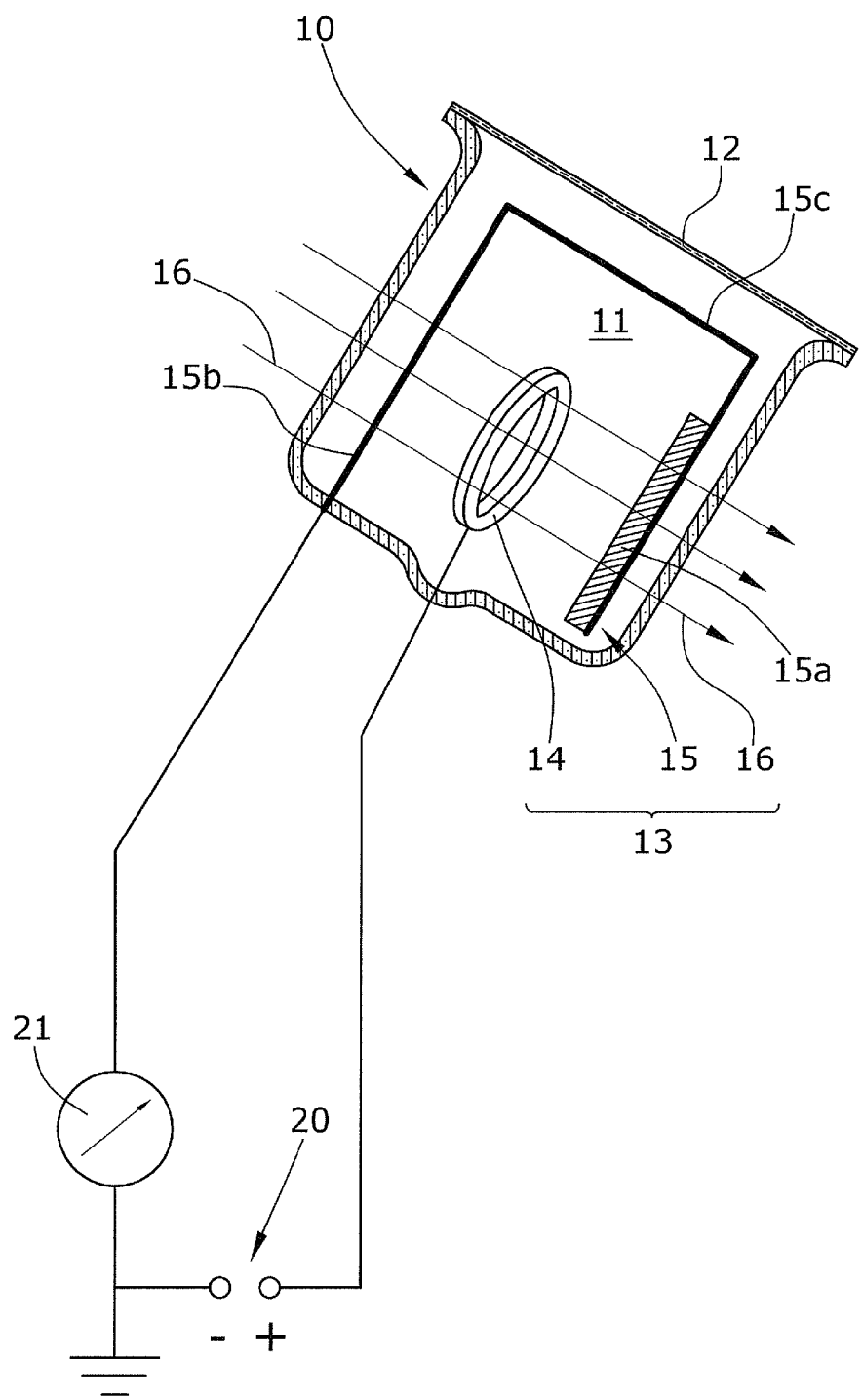

HELIUM SENSOR

BACKGROUND

1. Field of the Disclosure

The disclosure refers to a helium sensor comprising a detection chamber having a wall selectively permeable to a tracer gas, an ion getter pump having at least one cathode and at least one anode which are connected to a voltage source, and a magnetic field generator which generates a magnetic field extending across the detection chamber.

2. Discussion of the Background Art

A helium sensor of this type is described in DE 100 31 882 A1 (Leybold Vacuum GmbH). The detection chamber is made of glass and the wall selectively permeable to the tracer gas helium is a silicon disc provided with perforations that are each closed by means of a thin quartz membrane, the disc comprising a special heating. Such a gas sensor is also referred to as a quartz window sensor because of the nature of the selectively permeable wall. The gas atoms that have passed the selectively permeable wall are ionized in the detection chamber and are led to a cathode by an electrical field, where they are bound.

A similar helium sensor is described in DE 10 2004 034 381 A1 (Inficon GmbH).

SUMMARY

In a gas sensor of the present type, the detection of the tracer gas is based on the fact that a detectable current is generated in the electric circuit when the ionized gas atoms are discharged and are absorbed in the cathode. The detection limit of a helium sensor based on quartz window technology is limited by the existence of a base current with instabilities in the form of drift and noise. Noise is produced by the absorption/desorption process at the cathode of the cathode system, because it cannot be guaranteed that particles once absorbed will be retained permanently. Depending on the cathode temperature and the effect of impinging atoms, particles also leave the cathode again and create a certain instability of the base current, thereby creating noise. A drift is caused, substantially depending on the temperature, by the fact that due to the insufficient bonding forces in the event of a temperature change a new balance of adhesion and detachment occurs in the cathode material.

It is an object of the disclosure to provide a helium sensor of the above referenced type which has an improved detection limit.

The helium sensor of the present disclosure is characterized by the fact that at least one cathode of the cold cathode system includes beryllium.

In prior art the cathodes of the cold cathode system are made from titanium or tantalum. Titanium has an atomic mass of 48 amu and tantalum has an atomic mass of 181 amu. The atomic mass of helium is 4 amu. "amu" refers to the atomic mass of the core (atomic mass unit). The disclosure is based on the idea that at a high atomic mass of the cathode material, the light helium atoms impinging on the cathode will be reflected with high energy as neutral particles. A better binding of the helium atoms into the cathode can be achieved if the cathode material is a metal having an atomic mass similar to that of helium. The lightest metal that is still relatively good to handle industrially is beryllium with an atomic mass of 9 amu. The disclosure suggests manufacturing at least one cathode of the cold cathode system entirely or partly from beryllium.

The disclosure has the effect that not only the noise instability of the electric signal is reduced, but also that the base current that indicates the residual helium pressure is less by two or three orders of magnitude, since the permanent binding of the helium atoms pumped is obviously much better. Due to the lower base current, the thermal drift is reduced by the same amount, because of its percentage dependence on the vase current.

The detection limit of such a sensor, which is defined as the sum of drift (per minute) and noise (peak to peak), is thus improved correspondingly.

With the helium sensor of the disclosure, the cold cathode system can be designed either in Penning geometry or magnetron geometry. Both geometries are described in DE 100 31 882 A1 whose content is incorporated into the present specification by reference.

The following is a detailed description of an embodiment of the disclosure with reference to the sole drawing.

BRIEF DESCRIPTION OF THE DRAWINGS

The drawing schematically illustrates the structure of a quartz window helium sensor.

DETAILED DESCRIPTION OF THE PREFERRED EMBODIMENT

The helium sensor comprises a housing 10 made of glass that encloses an evacuated detection chamber 11. The housing 10 forms a parallelepiped or cylindrical body with a closed bottom wall. The opening opposite the bottom wall is closed with a selectively permeable wall 12. The wall 12 is a quartz window membrane as described in DE 100 31 882 A1. While the wall of the housing 10 is impermeable to gas, the wall 12 is selectively permeable to tracer gas which in the present case is helium.

The detection chamber 11 includes an ion getter pump 13. In a Penning geometry, the same comprises an annular anode 14 and a cathode 15 with two parallel cathode legs 15a, 15b. The anode 14 is of annular shape with the ring plane extending in parallel with the planes of the cathode legs 15a, 15b between which the anode is arranged. A magnetic field 16 extends orthogonally to this plane, which magnetic field is generated by a magnetic field generator (not illustrated) disposed outside the housing 10. The generator may be a permanent magnet, for instance. As an alternative, the arrangement can also be designed in a magnetron geometry, wherein the cathode (with an inverted magnetron: the anode) is disposed shaped as a rod in the central axis of a tube. With a magnetron, the pipe forms the anode (with an inverted magnetron: the cathode), the magnetic field extends axially in the tube and is generated in a manner known per se outside the tube by means of an annular magnet.

A high voltage of about 3,000 V is applied between the anode 14 and the cathode 15, which voltage is generated by a voltage source 20. The voltage source 20 is arranged outside the housing 10 and is connected to the cathode and the anode via current feedthrough means passing through the housing wall. The electric circuit comprises an ammeter 21 measuring the cathode current, the measured value hereof being a quantitative measure of the quantity of helium passing the wall 12.

The geometry of the ion getter pump illustrated in the drawing is a Penning geometry.

According to the disclosure, one leg 15a of the cathode 15 is made of beryllium. The opposite leg 15b of the cathode is made of titanium or another heavy metal, e.g. tantalum, as is the cathode sheet 15c connecting the two legs 15a and 15b. As measurements have shown, the same effect is also obtained with a structure wherein both cathode legs are made of beryllium or, in a magnetron geometry, the cathode is made of beryllium.

When helium atoms enter the detection chamber 11, the helium atoms are ionized and are accelerated towards the cathode 15 by means of the electric field. The helium ions are embedded in the light-weight structure of the beryllium cathode and are bound there. If one of the two cathode legs is made of a "heavy" metal, the neutralized ions are reflected as neutral particles and can thus easily penetrate into the opposite cathode of "light" metal, where they are absorbed. As a consequence, the percentage of reflected or unbound helium ions is reduced. Thereby, the base current is lowered (by the neutralization of "pumped" ions) and the noise signal is improved. Due to the reduced base current, the drift of this current is also correspondingly lower. The result is an improvement of the detection limit, i.e. of the smallest detectable helium partial pressure (resulting from the sum of drift and noise).

What is claimed is:

1. A helium sensor comprising a detection chamber with a wall selectively permeable to helium, an ion getter pump with at least one cathode and at least one anode, which are connected to a voltage source, and a magnetic field generator generating a magnetic field across the detection chamber, wherein at least one cathode consists essentially of beryllium.

2. The helium sensor of claim 1, wherein the ion getter pump has two cathode legs between which the at least one anode is arranged, one cathode leg contains beryllium and the other contains a heavy metal.

3. The helium sensor of claim 1, wherein said at least one cathode is entirely made of beryllium on the side facing the anode.

4. The helium sensor of claim 1, wherein the ion getter pump is designed in a Penning geometry.

5. The helium sensor of claim 1, wherein the ion getter pump is designed in a magnetron geometry or in an inverted magnetron geometry.

6. The helium sensor of claim 2, wherein the heavy metal comprises Ta or Ti.

7. The helium sensor of claim 1, wherein the at least one cathode contains the beryllium so that helium particles, once absorbed by the at least one cathode, are permanently retained.

8. A helium sensor comprising a detection chamber with a wall selectively permeable to helium, an ion getter pump with at least one cathode and at least one anode, and a magnetic field generator generating a magnetic field across the detection chamber, wherein the at least one cathode comprises a metal having an atomic mass similar to that of helium so that helium particles, once absorbed by the at least one cathode, are permanently retained.

9. The helium sensor of claim 8, wherein the metal comprises beryllium.

10. The helium sensor of claim 8, wherein the at least one cathode comprises two cathode legs between which the at least one anode is arranged, wherein a first cathode leg comprises the metal and a second cathode leg comprises a heavy metal.

11. The helium sensor of claim 10, wherein the metal comprises beryllium.

12. The helium sensor of claim 11, wherein the heavy metal comprises Ta.

13. The helium sensor of claim 11, wherein the heavy metal comprises Ti.

* * * * *